United States Patent
Lipson et al.

(10) Patent No.: US 7,536,213 B2
(45) Date of Patent: May 19, 2009

(54) REDUCTION IN SCATTERING FROM A TURBID MEDIUM BY PHOTO-BLEACHING

(75) Inventors: Jan Lipson, Cupertino, CA (US); Robert P. McNamara, San Jose, CA (US); Jeff Bernhardt, Santa Cruz, CA (US)

(73) Assignee: C8 Medisensors Inc., San Jose, CA (US)

( * ) Notice: Subject to any disclaimer, the term of this patent is extended or adjusted under 35 U.S.C. 154(b) by 0 days.

(21) Appl. No.: 11/764,123

(22) Filed: Jun. 15, 2007

(65) Prior Publication Data
US 2007/0291263 A1 Dec. 20, 2007

Related U.S. Application Data

(60) Provisional application No. 60/814,191, filed on Jun. 16, 2006.

(51) Int. Cl.
*A61B 5/1455* (2006.01)
*G01J 3/44* (2006.01)
*G01N 21/64* (2006.01)
*G01N 21/65* (2006.01)

(52) U.S. Cl. .................. 600/310; 600/316; 600/317; 600/476; 356/317

(58) Field of Classification Search ............ 600/310, 600/316, 318, 322, 476; 356/300, 301, 311, 356/317, 318
See application file for complete search history.

(56) References Cited

U.S. PATENT DOCUMENTS 6,650,915 B2 * 11/2003 Routt et al. .................. 600/319
7,057,721 B2 * 6/2006 Gardner et al. .............. 356/301

OTHER PUBLICATIONS

Wei-Chuan Shih et al., *Intrinsic Raman Spectroscopy Improves Analyte Concentration Measurements in Turbid Media*, Conference Paper—Biomedical Topical Meeting (BIO), Mar. 19, 2006, 3 pages.
Jun Wu et al., *Analytical model for extracting intrinsic fluorescence in turbid media*, Applied Optics, Jul. 1, 1993, pp. 3585-3595, vol. 32, No. 19.
Amnon Yariv, *Optical Electronics in Modern Communications*, 1997, pp. 171-175, Oxford University Press, U.S.A.
PCT International Search Report and Written Opinion, PCT/US2007/071483, Jul. 11, 2008.

* cited by examiner

*Primary Examiner*—Eric F Winakur
(74) *Attorney, Agent, or Firm*—Fenwick & West LLP

(57) ABSTRACT

A method is proposed whereby photo-bleaching is used not only to change the absorption and fluorescence of a sample but is also employed to change its scattering characteristics. When the compounds which are bleached are contained in regions wherein the real part of the index of refraction is greater than or equal to the average index of the medium, the bleaching will result in reduction in the scattering at wavelengths longer than the wavelength of the bleaching source. This reduction can be useful in measuring the concentration of analytes located at significant depths within turbid media.

9 Claims, 5 Drawing Sheets

REDUCTION IN SCATTERING FROM A TURBID MEDIUM BY PHOTO-BLEACHING

CROSS-REFERENCE TO RELATED APPLICATIONS

This application claims priority under 35 U.S.C. § 119(e) to U.S. Provisional Patent Application Ser. No. 60/814,191, "Reduction in Scattering from a Turbid Medium by Photo-Bleaching," filed Jun. 16, 2006, the subject matter of which is incorporated herein by reference in its entirety.

BACKGROUND OF THE INVENTION

1. The Field of the Invention

This invention relates generally to a method whereby optical scattering in a turbid medium may be reduced by photo-bleaching of substances which contribute to inhomogeneities in the index of refraction within the medium.

2. Background and Relevant Art

In many significant applications, a sample is illuminated with light, and information related to the composition of the sample is ascertained from transmitted, reflected, elastically scattered radiation, and/or inelastically scattered radiation. If it is desired to determine the concentration of substances which are deeply embedded in the sample, the presence of excessive elastic scattering can present insuperable difficulties. In such circumstances, the incident radiation will spread out in the sample, losing intensity in the process. In addition, light originating in the sample from inelastic processes such as fluorescence or Raman scattering will spread out from the point of origin, losing intensity upon transiting the turbid medium prior to exiting at the surface.

The aforementioned phenomenon of excessive scattering gives rise to practical problems in spectroscopy. In particular, the spreading of the radiation makes it necessary to image a source of significantly greater radial dimension than would be necessary in the absence of scattering, in order to collect a larger fraction of the desired radiation. For collecting optics of fixed focal length, there will be a spread in the angular distribution of the collected radiation which is proportional to the radial dimension of the spot being imaged. It is fundamental to many methods of wavelength discrimination that differing wavelengths incident at the same angle, cannot be distinguished from the same wavelengths incident at differing angles. The apparatus is incapable of distinguishing angular deviations from wavelength deviations. In consequence, a large spread in angles incident on the spectrometer reduces the resolution of the instrument accordingly.

Alternatively, to maintain spectral resolution, one could choose to increase the focal length of the collecting optics to limit the spread of angles, however, if one wants to preserve the collection efficiency, the diameter of the optics must be scaled up accordingly. It can be readily shown that the optics in the spectroscopic instrument must also be expanded proportionally. Hence, the size and cost of the whole system rises.

In yet another approach to this problem, one may divide up the field of view into multiple bins, each having a smaller spread in angle, and illuminate multiple spectrometers with a multiplicity of such beams. Again, the size and cost of the system will accordingly rise in proportion to the number of such bins.

The problem is particularly important in circumstances where the scattering process of interest is relatively weak in relation to the unwanted elastic scattering. An example of such a case is with Raman scattering which can be used to excite vibrational oscillations of molecules, which scattering spectra can then be used to ascertain the concentration of analytes of interest. Raman scattering is an exceptionally weak process. To obtain good signal to noise ratio in reasonable acquisition times, it is highly desirable to collect as much of the scattered radiation as possible. Yet it is not desirable to substantially degrade the resolution of the spectroscopic equipment. This is particularly important when there is a large broadband background of unwanted radiation, as is often the case where fluorescence from the sample is much larger than the Raman spectra of interest.

An excellent illustration of the problem may occur with biological samples such as human skin. Analytes of interest may primarily reside at some significant depth. As an example, if it is desired to noninvasively analyze the concentration of substances in blood, it is useful to use blood vessels of substantial diameter, but such vessels reside at depths of the order of 2 mm in most places. On the other hand, very substantial scattering generally transpires at depths significantly smaller than 2 mm. Radiation which is targeted at the blood vessel will suffer scattering in penetrating down to the vessel, and the desired scattered radiation from the blood will suffer further scattering prior to its emergence from the skin. To efficiently collect the radiation, it may be necessary to image an area with radius of the order of 1-2 mm. If good wavelength resolution is desired, such as of the order of 1 nm, and if good angular collection efficiency is further desired (such as of the order of f/1.4), it may be necessary to use optics that are several inches in diameter. Such optics are particularly unsuitable to situations where the device is desired to be portable, or worn by the subject.

SUMMARY OF THE INVENTION

These and other limitations are addressed by the present invention wherein a physical mechanism that will in general relate the absorption and scattering properties of a substance is used advantageously to reduce scattering by a process of selective photo-bleaching. Photo-bleaching is produced when a sample is exposed to optical radiation, and induced photo-chemical changes cause a reduction in the absorption of the incident radiation. In addition, it is shown that there should exist a relationship between absorption and scattering based on the observation that in any linear dissipative electromagnetic system, variations in the imaginary part of the index of refraction as a function of optical frequency must be accompanied by variations in the real part of the index. Elastic scattering is expected to be related to statistical fluctuations in the real part of the index. Absorption is well known to be directly related to the imaginary part of the index of refraction. It is therefore demonstrated that by modifying the absorption properties of an ensemble of substances using photo-bleaching, it is possible to engender substantial changes in the elastic scattering of such a sample.

In one aspect of the invention, an optical source which is used to generate useful spectra of analytes by an inelastic scattering process, is used simultaneously to induce reductions in the elastic scattering of the sample by photo-bleaching.

In a second aspect of the invention, an optical source of different wavelength is used to photo-bleach the sample advantageously, while a second optical source is used to generate the spectra of analytes by an inelastic scattering process.

In yet another aspect of the invention, the optical source used for photo-bleaching is activated prior to the activation of the source used to generate spectra of analytes, such that the fluorescence that is generated by the source which produces the photo-bleaching is not present when the spectra of the analytes is being gathered.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
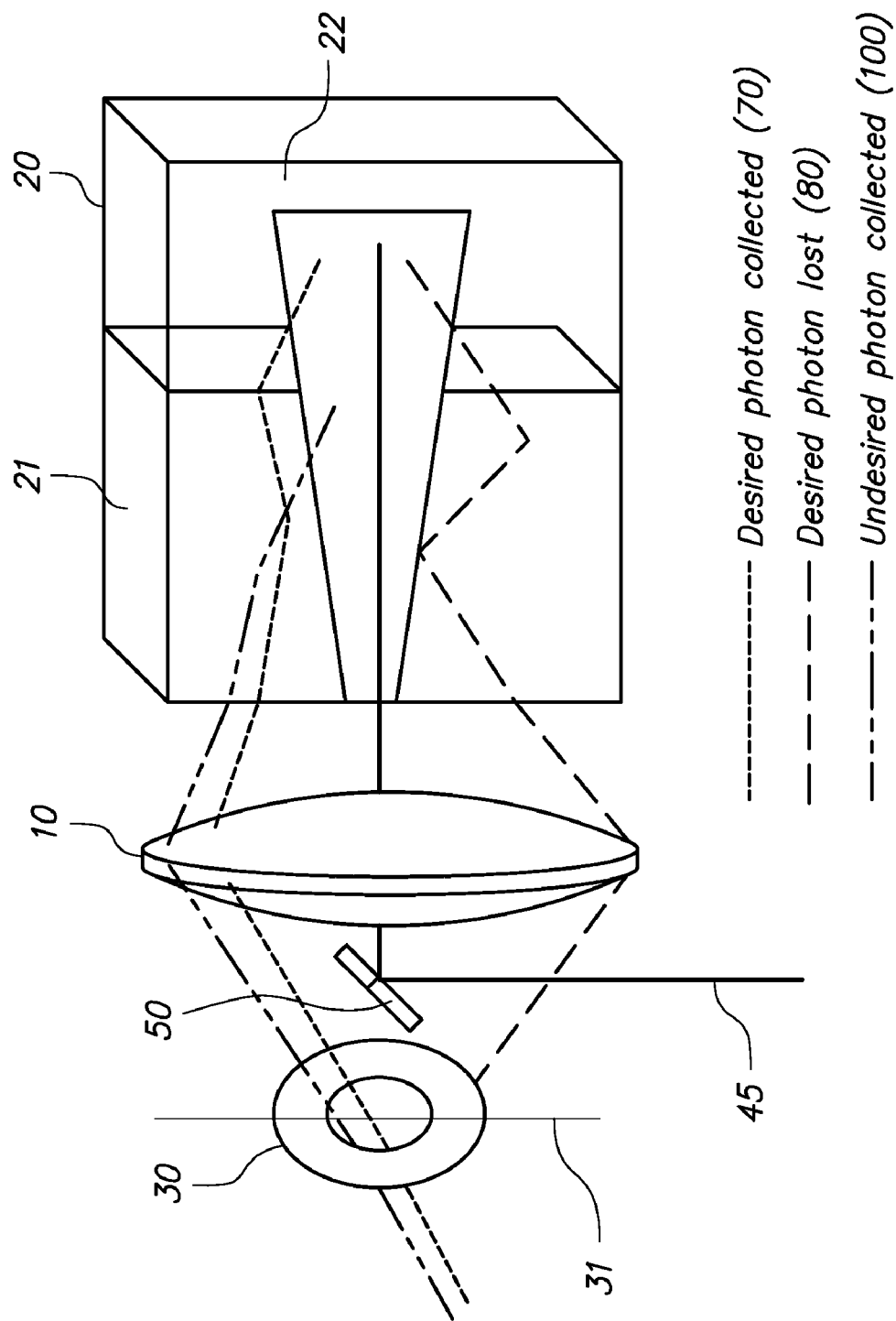
FIG. 1 (prior art) is a diagram of an optical scattering apparatus, wherein the effect of excessive scattering in the sample is illustrated.

In FIG. 1, a situation corresponding to the prior art is presented. The sample medium 20 in which a desired analyte is distributed is significantly turbid. This situation is considered analytically in, "Analytical Model for Extracting Intrinsic Fluorescence in Turbid Media," Jun Wu, Michael S. Feld, and Richard P. Rava, Applied Optics, Vol. 32, No. 19, p. 3589 (Jul. 1, 1993), which is incorporated herein by reference. The scattering from such a medium has two deleterious effects. In one instance a photon generated in the region 22 where the analyte resides, and which is generated by the analyte is not collected 80 due to the excessive scattering in the medium 20. Also shown, is the collection of an undesired photon 100 which originates from depths where the desired analyte is not present 21, and which is nevertheless collected. In the absence of scattering, it would be possible to focus the lens 10 on the desired region 22, and photons originating at positions far from the focus would have low probability of being collected. Due to the presence of scattering, it is not possible to as efficiently exclude these photons. In cases where there are substances whose spectra interfere with that of the analyte of interest and that reside outside of the region of interest, it is advantageous to exclude these spectra. In media with low scattering and where the interfering substance resides in a volume distinct from that of the analyte, this is possible by focusing, but when scattering is excessive, this capability is impaired.

In order to understand the proper design of the preferred embodiments it is first useful to create a theoretical framework for the effect of photo-bleaching on scattering.

The starting point for the analysis are the Kramers-Kronig relations, a treatment of which can be found in Optical Electronics in Modern Communications, by A. Yariv, $5^{th}$ edition, Oxford University Press, 1997, p. 171, and, in more detail, in Appendix A, which are incorporated herein by reference.

The Kramers-Kronig relations can be written as:

$$\chi'(\omega) = \frac{1}{\pi} P.V. \int_{-\infty}^{\infty} \chi''(\omega')/(\omega' - \omega) d\omega' \quad (1)$$

and $$\chi''(\omega) = \frac{1}{\pi} P.V. \int_{-\infty}^{\infty} \chi'(\omega')/(\omega' - \omega) d\omega' \quad (2)$$

where $\chi'(\omega)$ is the real part of the electric susceptibility as a function of the optical frequency, $\omega$, $\chi''(\omega)$ is the imaginary part of the electric susceptibility, and P.V. is the Cauchy principle value of the integral which follows.

We can relate the absorption coefficient of the sample, $\gamma(\omega)$, to the imaginary part of the electrical susceptibility as follows:

$$\gamma(\omega) = -\frac{\omega}{n} \chi''(\omega) \quad (3)$$

where n is the index of refraction of the medium. We also can relate the change in the real part of the index of refraction, $\Delta n$, to the real part of the electric susceptibility as follows:

$$\Delta n = \chi'(\omega)/2n \quad (4)$$

Equations (1) to (4) apply to a broad range of linear dissipative electromagnetic media. It is instructive to consider a simple case of a monochromatic wave propagating through an atomic medium, with $N_2$ atoms per unit volume in level 2, and $N_1$ atoms per unit volume in level 1, with $N_2 < N_1$ such that the medium will be absorbing. We consider the case of a Lorentzian line shape, for which it can be shown that:

$$\chi''(\omega) = \frac{2\pi^2 (N_1 - N_2) c^3 \tau}{\omega^3 n \tau_{spont}} \frac{1}{4\pi^2 + (\omega - \omega_o)^2 \tau^2} \quad (5)$$

where c is the speed of light in vacuum, $\tau_{spont}$ is the spontaneous emission lifetime, $\omega_o$ is the frequency of the Lorentzian resonance, and $\tau = 2/\Delta v$, where $\Delta v$ is the Lorentzian linewidth. Equation (5) is principally valid in the regime where $\omega \sim \omega_o$. In such a case, equation (1) yields:

$$\chi'(\omega) = \frac{(N_1 - N_2) c^3 \tau^2}{\omega^3 n \tau_{sp}} \frac{\pi(\omega - \omega_o)}{4\pi^2 + (\omega - \omega_o)^2 \tau^2} \quad (6)$$

Figure 2:
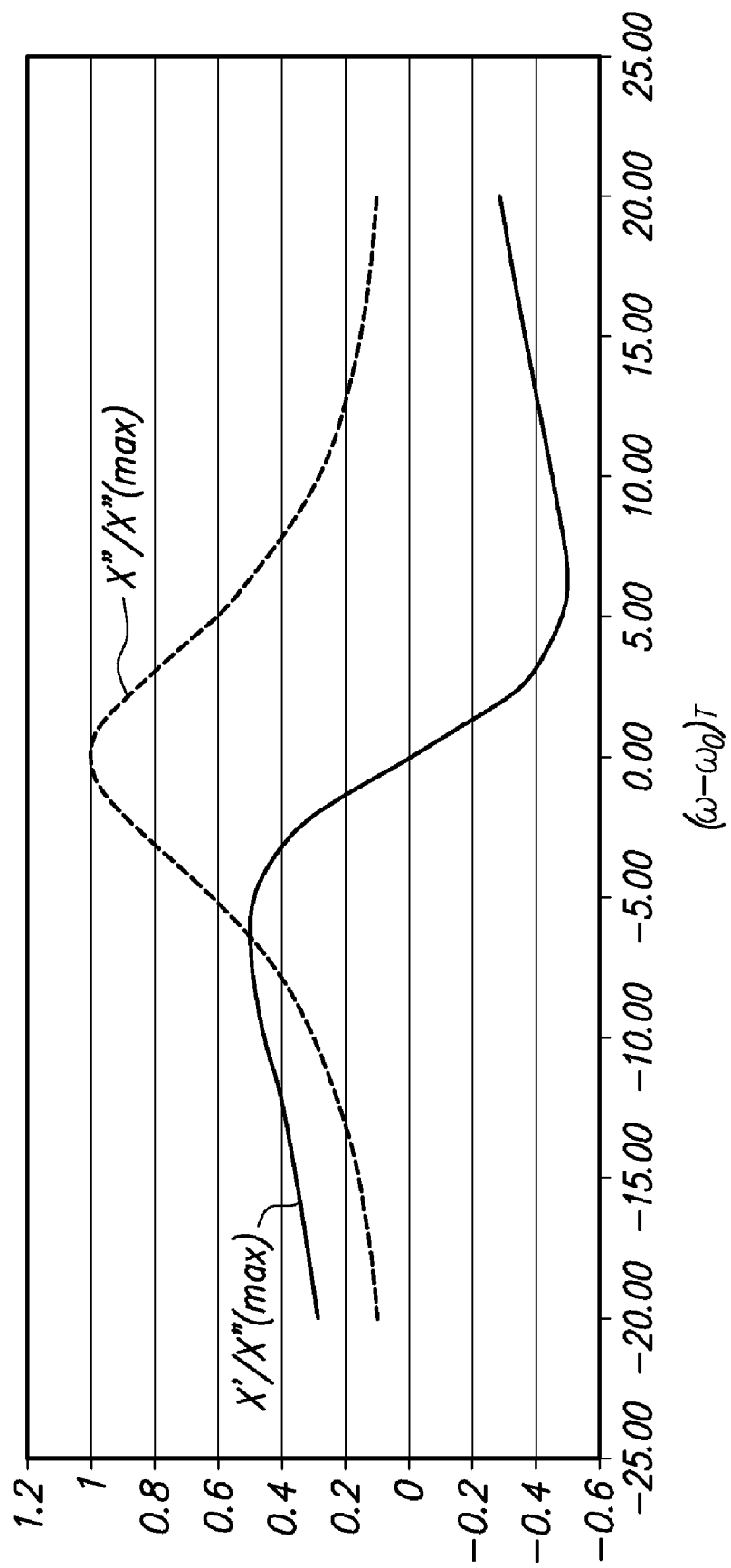
FIG. 2 illustrates the relationship between the real and imaginary parts of the susceptibility of a material for a linear dissipative electromagnetic system.

Referring to FIG. 2, a plot is shown for both the real and imaginary parts of the electrical susceptibility with normalization to the maximum value of the imaginary susceptibility, $\chi''_{max}$ (the maximum value occurs at $\omega = \omega_o$). The abscissa in FIG. 2 is in dimensionless units of $(\omega - \omega_o)\tau$. It can be seen that for frequencies $> \omega_o$, the contribution to the real part of the index is negative and for frequencies $< \omega_o$, the contributions are positive. The general shape of these functions will be preserved for any linear dissipative resonant systems. If there are multiple substances possessing different resonances, the results will be additive.

The case in which inelastic scattering processes give rise to spectra that are red-shifted with respect to the frequency of the excitation source is particularly important. If there is an ensemble of absorbing substances, each will contribute to the elevation of the real part of the electrical susceptibility and hence to the real part of the index of refraction at wavelengths longer than the excitation wavelength. Any mechanism which causes a change in the absorption will have a corresponding effect on the real part of the index of refraction. Photo-bleaching is precisely such a mechanism, wherein the absorption associated with substances that are bleached, decreases with time.

Inhomogeneities in the real part of the index of refraction will give rise to scattering of optical radiation. In general, the magnitude of the scattering will scale as $(n_1-n_0)^2$, where $n_1$ is the index of the inhomogeneity in the medium and $n_0$ is the average index of the medium. Molecules which absorb radiation may be localized in particular structures in biological tissue. An example would be that hemoglobin is localized on red blood cells. The areas in which these absorbing substances are localized may have refractive indices which are either more or less than the average index of the medium. It is useful to consider different cases. The first example is one in which the index of the regions in which the absorbing substance is localized, when evaluated in the absence of the absorbing substance, is greater than or equal to the average index of the medium. If there are systematic positive contributions to $n_1$ from the absorbing substances, by the mechanism already described, the scattering will thereby increase. A reduction in the absorption, which is effected by means of photo-bleaching, will then result in a decrease in scattering because the positive contributions to the real part of the index will thereby be reduced.

In the second example we consider the case where the index of the regions in which the absorbing substance is localized is less than that of the average index of the medium. In this case, systematic increases in the index due to the presence of the absorbing substances will cause the scattering to decrease, provided that the increase due to absorption is less than the initial difference between the index of the aforementioned regions and the average index.

It is therefore seen that it is possible to decrease or increase scattering by photo-bleaching, depending upon the scenario for the indices. It is, however, observed in at least one important case that the scattering can be decreased. An example of such a decrease has been reported for the case of exposure of human skin to near IR laser radiation (see for example, "Intrinsic Raman Spectroscopy Improves Analyte Concentration Measurements," Wei-Chuan Shi, Kate L. Bechtel, and Michael S. Feld, in Technical Digest, Biomedical Optics Topical Meeting, March 19-22, Fort Lauderdale Fla., paper MC7, which is incorporated herein by reference).

Figure 3:
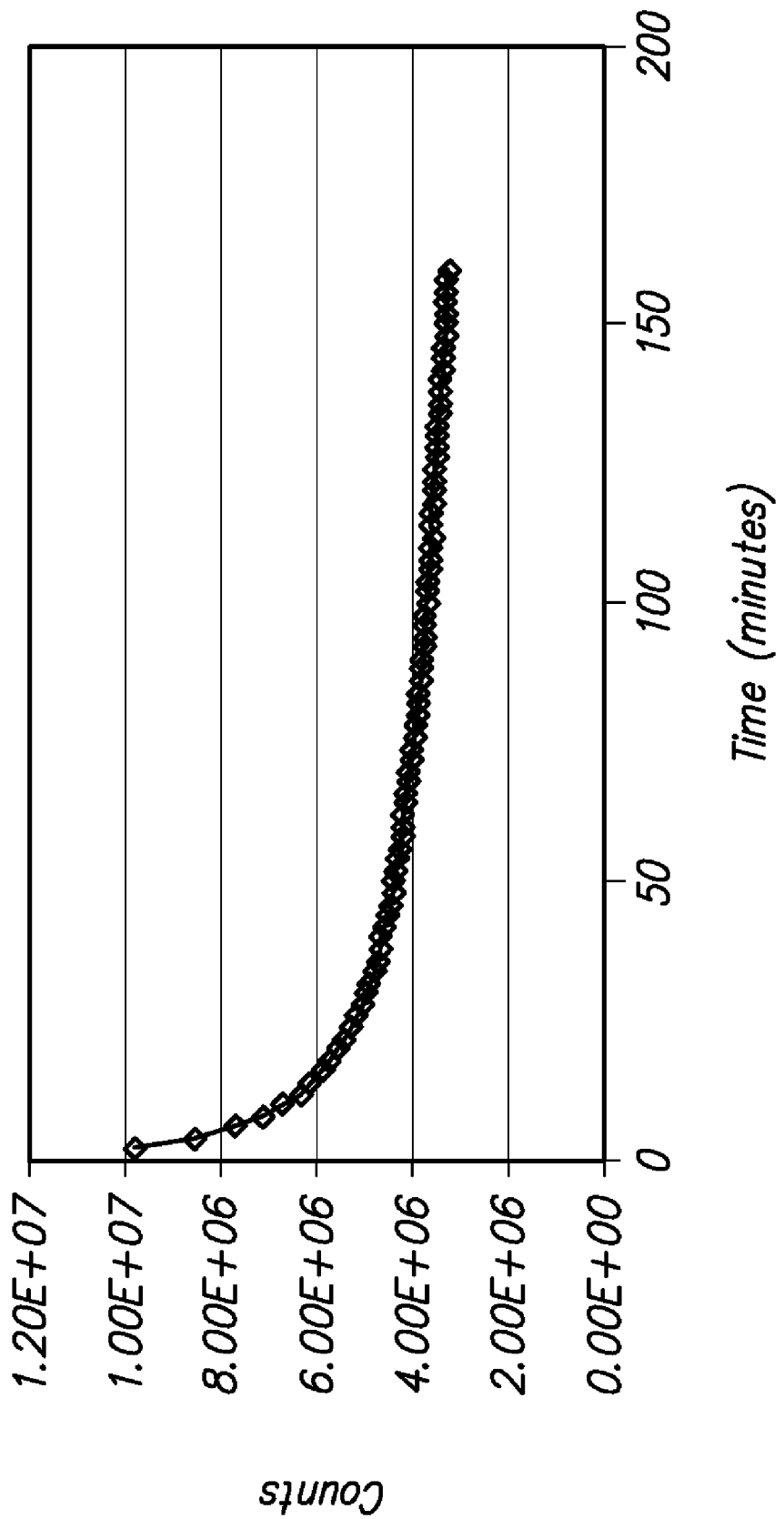
FIG. 3 is a graph of fluorescence emission from human skin at a specific wavelength, $\lambda_F$, displaced to the red side of the spectrum from the illuminating wavelength, $\lambda_I$, as a function of time. For this example, $\lambda_I$ is equal to 785 nm.

In FIG. 3, the fluorescence of human skin at a specific wavelength $\lambda_F$, displaced to the red side of the spectrum from the illuminating wavelength, $\lambda_I$, as a function of time is presented for the case of an exposure of the skin sample to 450 mW of 785 nm laser radiation. A large decrease in the fluorescence is observed over the period. The fluorescence can be presumed to scale with the absorption, as absorption is the mechanism from which it is generated. Hence, the absorption has also decreased substantially with time. In consequence, the contribution of the absorption to the real part of the index of refraction has also decreased.

Figure 4:
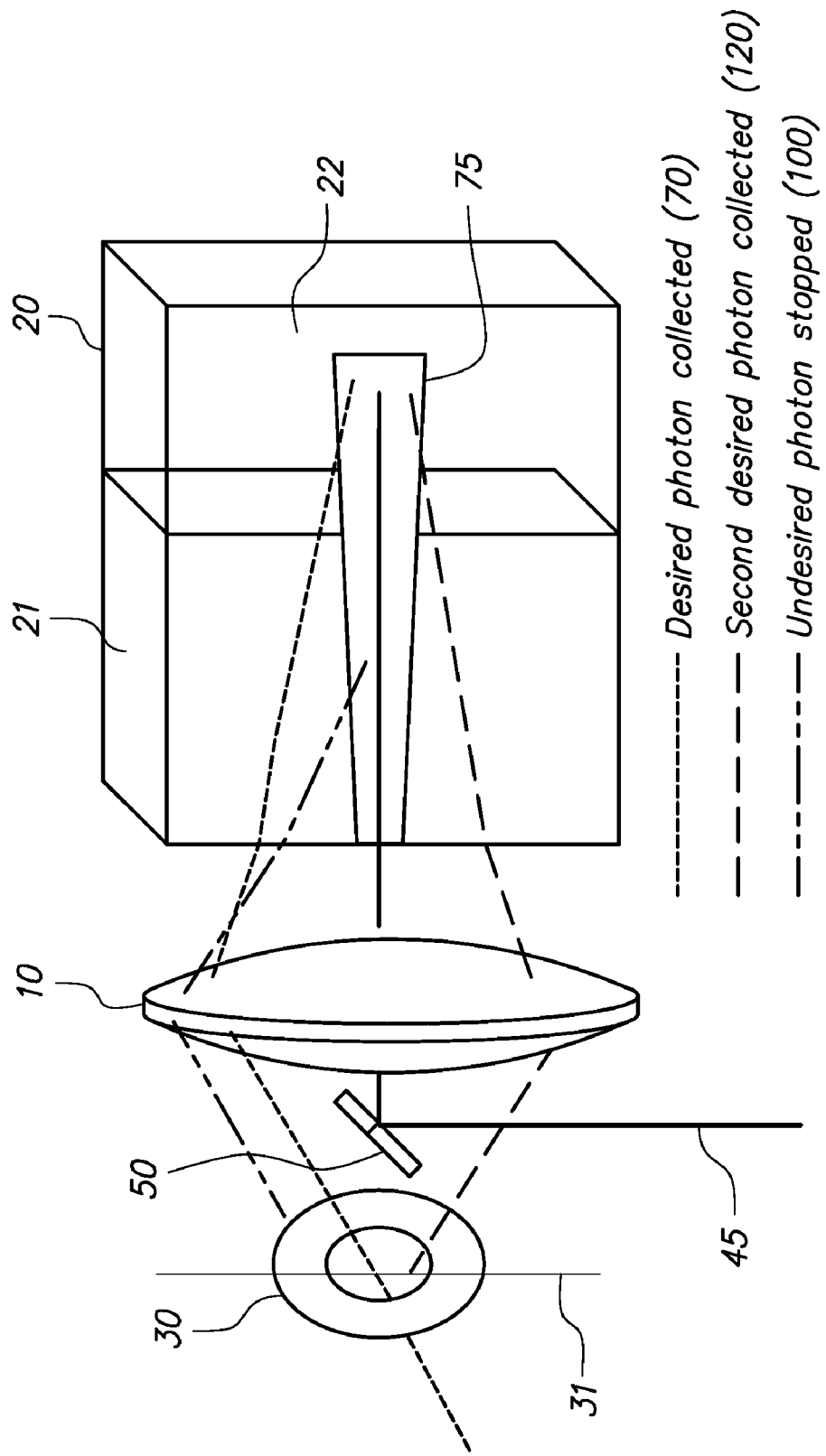
FIG. 4 is a block diagram of one embodiment of the invention wherein a single optical source is used for photo-bleaching and the generation of analyte spectra.

In FIG. 4, a preferred embodiment is presented in which the laser which is used for inelastic excitation of the desired spectrum, is also used to photo-bleach the sample so as to change the scattering within the sample. The inelastic excitation processes can include but are not limited to fluorescence and Raman scattering. The sample 20 may consist of any composite of materials which contains a photo-bleachable substance that is not uniformly distributed throughout the sample 20. For example, some or all of the analyte of interest may reside at a depth greater than the effective elastic scattering length of the sample given by $1/u_s'$, where $u_s'$ is the isotropic scattering coefficient of the sample.

In FIG. 4, the reduction of scattering is represented by a reduced cone angle 75 made by the entering laser beam 45 that reflects from mirror 50 through lens 10. In addition, the photons which are generated by the inelastic process undergo less scattering. In this example, a second photon 120 which was desired but not collected in FIG. 1, is shown passing through the aperture 30 located at the image plane 31. A photon not desired to be collected 100 is shown being blocked by the aperture. The improvements are a consequence of reduced scattering. The area which is photo-bleached 75 corresponds to the region where the laser beam energy is primarily confined. As the scattering drops, the cone angle of the beam will diminish and the area will become smaller, making the bleaching in that volume progressively more complete.

The embodiment of FIG. 4 illustrates the case when the sample has the property wherein, the average of the real part of the index of refraction of the medium is less than the real part of the index of refraction of the regions in which the absorption is localized, and where said latter index is evaluated in the absence of the absorbing substance. In this case, the reduction in absorption by photo-bleaching will be accompanied by a decrease in scattering.

When the sample comprises human skin, it is found that illumination with about 450 mW of optical power at 785 nm, in a spot of approximately 1 mm in diameter can produce useful bleaching. As the bleaching scales with the power density a smaller or larger spot would require reduced or increased power respectively for the bleaching to proceed at a similar rate.

In yet another preferred embodiment, the optical source used for photo-bleaching and the source used for inelastic excitation of a desired spectrum are not identical. A schematic diagram of this arrangement is presented in FIG. 5. It is possible when the sources are distinct to choose different wavelengths of emission for each. In a particularly preferred embodiment, the wavelength of the source which is used for bleaching is chosen to be shorter than the wavelength of the source used for spectral excitation. It is expected, in many instances, that the bleaching will proceed more efficiently at shorter wavelengths because the energy of the photons will be greater. In one embodiment, the difference in emission wavelengths between the source used for photo-bleaching and the source used for inelastic excitation of a desired spectrum as expressed in wavenumbers is greater than 1000 cm$^{-1}$. It has been observed by the inventors that bleaching at 670 nm of human skin is about three times more efficient than bleaching at 830 nm in the spectral region 830 to 960 nm. In consequence, illumination with 100 mW of 670 nm radiation in a 1 mm diameter spot can provide useful levels of bleaching in human skin.

In some instances, it is possible to use the two sources such that both may generate useful spectra, and one or both will also perform bleaching. A good example is found in the Raman spectroscopy of human skin wherein it is desired to ascertain not only the concentration of one or more analytes, but also the amount of water present. Water is conveniently measured at a wavenumber of about 3400 cm$^{-1}$, however, the spectra of other analytes usually lie at much smaller wavenumber (300-1700 cm$^{-1}$ is most typical for human skin). In consequence, if the same source is used to measure both the spectral lines of the analytes and that of water, the water line may lie outside the spectral range of a single spectrometer which has been optimized for observing the other analytes. If, however, a shorter wavelength is chosen for the bleaching source, that source can also be used to shift the water line to be in range of the spectrometer. That is because the Raman spectra occur at fixed intervals with respect to the excitation source, and hence, the shifting of the wavelength of the excitation source will correspondingly shift the wavelengths of the Raman spectra. Of course, the same principle may be applied to other substances besides water that have useful Raman lines at wavenumbers larger than those of other analytes of interest.

Figure 5:
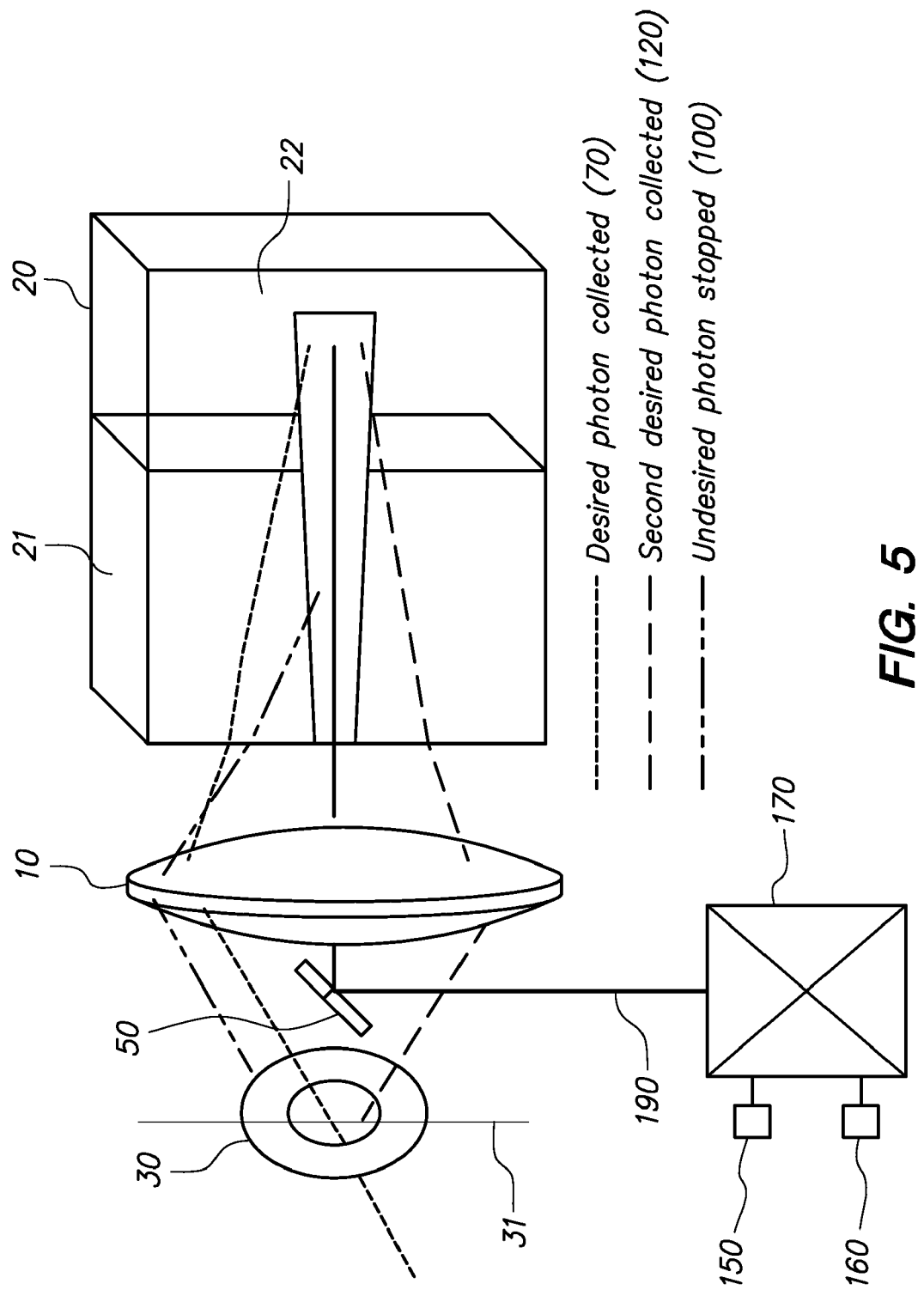
FIG. 5 is a block diagram of another embodiment of the invention wherein two distinct optical sources are used for photo-bleaching and analyte spectra generation.

The sources 150, 160 used in FIG. 5 can be selected by an optical switch 170. In principle, the optical switch can choose either source, both, or neither, and the concept can be extended to any number of sources that make up the optical power 190 that enters the sample 20. In a variant of this arrangement, the two sources 150, 160 are always combined optically (as with a passive wavelength multiplexing device), but either source or both can be activated by appropriate electrical excitation. Either the switch 170 or passive combiner can be, for example, a free-space device where the optical radiation is transmitted in air, or, for example, these can be fiber-optic devices.

The invention claimed is:

1. A method for reducing elastic scattering from a sample comprising an analyte residing at a significant depth in the sample and a non-uniformly distributed photo-bleachable substance, the method comprising:
    photo-bleaching the non-uniformly distributed photo-bleachable substance in the sample to induce a reduction in elastic scattering in the sample;
    generating analyte spectra from inelastic scattering from the sample, wherein some or all of the analyte resides at a depth in the sample greater than an effective elastic scattering length of the sample, wherein the effective elastic scattering length is $1/u_s'$, wherein $u_s'$ is an isotropic scattering coefficient of the sample, and wherein the inelastic scattering is relatively weak in relation to the elastic scattering; and
    collecting the analyte spectra, wherein a sufficient amount of the analyte resides at the depth in the sample greater than an effective elastic scattering length of the sample such that the collected analyte spectra has a higher signal to noise ratio than without photo-bleaching.

2. The method of claim 1, wherein the inelastic scattering comprises fluorescence.

3. The method of claim 1, wherein the inelastic scattering comprises Raman scattering.

4. The method of claim 1, wherein the step of photo-bleaching is performed by a source of optical radiation that performs the step of generating analyte spectra.

5. The method of claim 1, wherein the step of photo-bleaching is performed by a source of optical radiation that operates at a different wavelength than a source that performs the step of generating analyte spectra.

6. The method of claim 5, wherein the source that performs the step of generating analyte spectra operates at a longer wavelength than the source performing photo-bleaching.

7. The method of claim 5, wherein the source of optical radiation that performs photo-bleaching operates at a first wavelength, and the source of optical radiation that performs the step of generating analyte spectra operates at a second wavelength, and difference between the first and second wavelengths as expressed in wavenumbers is greater than 1000 cm$^{-1}$.

8. The method of claim 1, wherein the step of photo-bleaching occurs before the step of generating analyte spectra.

9. The method of claim 1, wherein the sample comprises human skin.

* * * * *